United States Patent [19]
Gaffar et al.

[11] Patent Number: 5,466,437
[45] Date of Patent: * Nov. 14, 1995

[54] ANTIBACTERIAL ANTIPLAQUED ORAL COMPOSITION MOUTHWASH OR LIQUID DENTIFRICE

[75] Inventors: Abdul Gaffar, Princeton; Nuran Nabi, No. Brunswick; John Afflitto, Brookside, all of N.J.; Orum Stringer, Yardley, Pa.

[73] Assignee: Colgate Palmolive Company, Piscataway, N.J.

[ * ] Notice: The portion of the term of this patent subsequent to Jan. 16, 2007, has been disclaimed.

[21] Appl. No.: 161,013

[22] Filed: Dec. 3, 1993

Related U.S. Application Data

[62] Division of Ser. No. 961,976, Oct. 16, 1992, Pat. No. 5,294,431, which is a division of Ser. No. 398,592, Aug. 28, 1989, Pat. No. 5,188,821, which is a continuation-in-part of Ser. No. 291,712, Dec. 29, 1988, Pat. No. 4,894,220, and a continuation-in-part of Ser. No. 346,258, May 1, 1989, Pat. No. 5,043,154, which is a continuation of Ser. No. 8,901, Jan. 30, 1987, abandoned, said Ser. No. 291,712 is a continuation-in-part of Ser. No. 8,901.

[51] Int. Cl.$^6$ ............................. A61K 7/16; A61K 7/18; A61K 7/26

[52] U.S. Cl. .................... 424/52; 424/49; 424/58
[58] Field of Search ........................... 424/49–88

[56] References Cited

U.S. PATENT DOCUMENTS

| | | | |
|---|---|---|---|
| 3,429,963 | 2/1969 | Shedlorsky | 424/56 |
| 4,022,880 | 5/1977 | Vinson et al. | 424/49 |
| 4,894,220 | 1/1990 | Nabi et al. | 424/52 |
| 4,980,153 | 12/1990 | Jackson et al. | 424/52 |
| 5,032,385 | 7/1991 | Reed et al. | 424/49 |
| 5,032,386 | 7/1991 | Gaffar et al. | 424/49 |
| 5,037,635 | 8/1991 | Nabi et al. | 424/52 |
| 5,188,821 | 2/1993 | Gaffar et al. | 424/52 |
| 5,192,531 | 3/1993 | Gaffar et al. | 424/52 |
| 5,288,480 | 2/1994 | Gaffar et al. | 424/52 |
| 5,294,431 | 3/1994 | Gaffar et al. | 424/52 |

Primary Examiner—Shep Rose
Attorney, Agent, or Firm—Robert L. Stone; Robert C. Sullivan

[57] ABSTRACT

An oral composition mouthwash or liquid dentifrice containing an aqueous vehicle acceptable vehicle, a substantially water-insoluble noncationic antibacterial antiplaque agent, such as 2,4,4'-trichloro-2'-hydroxy-diphenyl ether (triclosan) and an antibacterial-enhancing agent which enhances delivery of said antibacterial agent to, and retention thereof on, oral surfaces.

25 Claims, No Drawings

ANTIBACTERIAL ANTIPLAQUED ORAL COMPOSITION MOUTHWASH OR LIQUID DENTIFRICE

This application is a Division of application Ser. No. 07/961,976, filed Oct. 16, 1992, now U.S. Pat. No. 5,294,431, granted Mar. 15, 1994, which is a Division of application Ser. No. 07/398,592, filed Aug. 28, 1989, now U.S. Pat. No. 5,188,821, granted Feb. 23, 1993, which is a continuation-in-part of application Ser. No. 07/291,712, filed Dec. 29, 1988 and now U.S. Pat. No. 4,894,220, granted Jan. 16, 1990, and of application Ser. No. 07/346,258 filed May 1, 1989, now U.S. Pat. No. 5,043,154, granted Aug. 27, 1991 which are respectively a continuation-in-part and a continuation of application Ser. No. 07/008901, filed Jan. 30, 1987 now abandoned.

This invention relates to an antibacterial antiplaque oral composition mouthwash or liquid dentifrice. More particularly, it relates to an oral composition mouthwash or liquid dentifrice containing a substantially water-insoluble noncationic antibacterial agent effective to inhibit plaque.

Dental plaque is a soft deposit which forms on teeth as opposed to calculus which is a hard calcified deposit on teeth. Unlike calculus, plaque may form on any part of the tooth surface, particularly including at the gingival margin. Hence, besides being unsightly, it is implicated in the occurence of gingivitis.

Accordingly, it is highly desirable to include antimicrobial agents which have been known to reduce plaque in oral compositions. Frequently, cationic antibacterial agents have been suggested. Moreover, in U.S. Pat. No. 4,022,880 to Vinson et al, a compound providing zinc ions as an anticalculus agent is admixed with an antibacterial agent effective to retard the growth of plaque bacteria. A wide variety of antibacterial agents are described with the zinc compounds including cationic materials such as guanides and quaternary ammonium compounds as well as non-cationic compounds such as halogenated salicylanilides and halogenated hydroxydiphenyl ethers. The noncationic antibacterial antiplaque halogenated hydroxydiphenyl ether, triclosan, has also been described in combination with zinc citrate trihydrate in European Patent Publication 0161,899 to Saxton et al. Also, in European Patent Publication 0271,332 to Davis, mouthwash containing triclosan and in a carrier system containing a solubilizing agent such as propylene glycol is disclosed.

The cationic antibacterial materials such as chlorhexidine, benzthonium chloride and cetyl pyridinium chloride have been the subject of greatest investigation as antibacterial antiplaque agents. However, they are generally not effective when used with anionic materials. Noncationic antibacterial materials, on the other hand, can be compatible with anionic components in an oral composition.

However, oral compositions typically are mixtures of numerous components and even such typically neutral materials as humectants can affect performance of such compositions.

Moreover, even noncationic antibacterial antiplaque agents may have limited antiplaque effectiveness with commonly employed materials such as polyphosphate anticalculus agents which are disclosed together in British Patent Publication 2200551 of Gaffar et al and EP 0251591 of Jackson et al. In commonly assigned Ser. No. 398,605 filed on Aug. 25, 1989, titled "Antibacterial, Antiplaque Anticalculus Oral Composition", it is shown that the antiplaque effectiveness is greatly enhanced by including an antibacterial-enhancing agent (AEA) which enhances the delivery of said antibacterial agent to, and retention thereof on, oral surfaces and providing optimized amounts and ratios of polyphosphate and AEA.

Further, even when polyposphate anticalculus agent is not present as shown in patent applications commonly assigned 398,606, 398,566, and 399,699 each filed on Aug. 25, 1989, antiplaque effectiveness on soft oral tissue is optimized in dentifrices containing the noncationic antibacterial agent and said AEA.

It is an advantage of this invention that an oral composition mouthwash or liquid dentifrice is obtained in which substantially water-insoluble noncationic antibacterial agent is solubilized to provide substantial antiplaque effectiveness in the presence of said AEA.

It is an advantage of this invention that the said AEA enhances the delivery and retention of small but effective antiplaque amount of the antibacterial agent on teeth and on soft oral tissues.

It is a further advantage of this invention that an antiplaque oral composition is provided which is directly or indirectly effective to reduce the occurrence of gingivitis.

Additional advantages of this invention will be apparent from consideration of the following specification.

In accordance with certain of its aspects, this invention relates to an oral composition dentifrice comprising in an orally acceptable vehicle, an effective antiplaque amount of a substantially water insoluble noncationic antibacterial agent, and about 0.05–4% by weight of said AEA, wherein said oral composition comprises a solubilizing material for said antibacterial agent in amount sufficient to dissolve said antibacterial agent in saliva.

Typical examples of water insoluble noncationic antibacterial agents which are particularly desirable from considerations of antiplaque effectiveness, safety and formulation are:

Halogenated Diphenyl Ethers

2',4,4'-trichloro-2'-hydroxy-diphenyl ether (Triclosan)
2,2'-dihydroxy-5,5'-dibromo-diphenyl ether.
Halogenated Salicylanilides 4',5-dibromosalicylanilide
3,4',5-trichlorosalcylanilide
3,4',5-tribromosalicylanilide
2,3,3',5-tetrachlorosalicylanilide
3,3,3',5-tetrachlorosalicylanilide
3,5-dibromo-3'-trifluoromethyl salicylanilide
5-n-octanoyl-3'-trifluoromethyl salicylanilide
3,5-dibromc-4'-trifluoromethyl salicylanilide
3,5-dibromo-3'-trifluoro methyl salicylanilide (Fluorophene)
Benzoic Esters Methyl-p-Hydroxybenzoic Ester
Ethyl-p-Hydroxybenzoic Ester
Propyl-p-Hydroxybenzoic Ester
Butyl-p-Hydroxybenzoic Ester
Halogenated Carbanilides 3,4,4'-trichlorocarbanilide
3-trifluoromethyl-4,4'-dichlorocarbanilide
3,3,4'-trichlorocarbanilide
Phenolic Compounds (including phenol and its homologs, mono- and poly-alkyl and aromatic halo (e.g. F, Cl, Br, I)-phenols, resorcinol and catechol and their derivatives and bisphenolic compounds). Such compounds include inter alia:
Phenol and its Homologs henol
Methyl-Phenol
Methyl-Phenol -continued Methyl-Phenol
Ethyl-Phenol
2,4-Dimethyl-Phenol
2,5-Dimethyl-Phenol
3,4-Dimethyl-Phenol
2,6-Dimethyl-Phenol
4-n Propyl-Phenol
4-n-Butyl-Phenol
4-n-Amyl-Phenol
4-tert-Amyl-Phenol
4-n-Hexyl-Phenol
4-n-Heptyl-Phenol
2-Methoxy-4-(2-Propenyl)-Phenol (Eugenol)
2-Isopropyl-5-Methyl-Phenol (Thymol)
Mono- and Poly-Alkyl and Aralkyl Halophenols Methyl-p-Chlorophenol
Ethyl-p-Chlorphenol
n-Propyl-p-Chlorophenol
n-Butyl-p-Chlorophenol
n-Amyl-p-Chlorophenol
sec-Amyl-p-Chlorophenol
n-Hexyl-p-Chloraphenol
Cyclohexyl-p-Chlorophenol
n-Heptyl-p-Chlorophenol
n-Octyl-p-Chloraphenol
O-Chlorcphenol
Methyl-o-Chlorophenol
Ethyl-o-Chlorophenol
n-Propyl-o-Chloraphenol
n-Butyl-o-Chlorophenol
n-Amyl-o-Chlorophenol
tert-Amyl-o-Chlorophenol
n-Hexyl-o-Chlarophenol
n-Heptyl-o-Chloropenol
p-Chlorophenol
o-Benzyl-p-Chlorophenol
o-Benzyl-m-methyl-p-Chlorophenol
o-Benzyl-m, m-dimethyl-p-Chlorophenol
o-Phenylethyl-p-Chlorophenol
o-Phenylethyl-m-methyl-p-Chlorophenol
3-Methyl-p-Chlorophenol
3,5-Dimethyl-p-Chlorophenol
6-Ethyl-3-methyl-p-Chlorophenol
6-n-Propyl-3-methyl-p-Chlorophenol
6-iso-propyl-3-methyl-p-Chlorophenol
2-Ethyl-3,5-dimethyl-p-Chlorophenol
6-sec Butyl-3-methyl-p-Chlorophenol
2-iso-Propyl-3,5-dimethyl-p-Chlorophenol
6-Diethylmethyl-3-methyl-p-Chlorophenol
6-iso-Propyl-2-ethyl-3-methyl-p-Chlorophenol
2-sec Amyl-3,5-dimethyl-p-Chlorophenol
2-Diethylmethyl-3,5-dimethyl-p-Chlorophenol
6-sec Octyl-3-methyl-p-Chlorophenol
p-Bromophenol
Methyl-p-Bromophenol
Ethyl-p-Bromophenol
n-Propyl-p-Bromophenol
n-Butyl-p-Bromophenol
n-Amyl-p-Bromophenol
sec-Amyl-p-Bromophenol
n-Hexyl-p-Bromophenol
cyclohexyl-p-Bromophenol
o-Bromophenol
tert-Amyl-o-Bromophenol
n-Hexyl-o-Bromophenol
n-Propyl-m,m-Dimethyl-o-Bromophenol
2-Phenyl Phenol
4-Chlora-2-methyl phenol
4-chloro-3-methyl phenol
4-chloro-3,5-dimethyl phenol
2,4-dichloro-3,5-dimethyl phenol
3,4,5,6-tetrabromo-2-methylphenol
5-methyl-2-pentylphenol
4-isopropyl-3-methylphenol
5-chloro-2-hydroxydiphenyl methane
Resorcinol and Its Derivatives Resorcinol -continued Methyl-Resorcinol
Ethyl-Resorcinol
n-Propyl-Resorcinol
n-Butyl-Resorcinol
n-Amyl-Resorcinol
n-Hexyl-Resorcinol
n-Heptyl-Resorcinol
n-Octyl-Resorcinol
n-Nonyl-Resorcinol
Phenyl-Resorcinol
Benzyl-Resorcinol
Phenylethy-Resorcinol
Phenylpropyl-Resorcinol
p-Chlorobenzyl-Resorcinol
5-Chloro-2,4-Dihydroxydiphenyl Methane
4'-Chloro-2,4-Dihydroxydiphenyl Methane
5-Bromo-2,4-Dihydroxydiphenyl Methane
4"-Bromo-2,4-Dihydroxydiphenyl Methane
Bisphenolic Compounds Bisphenol A
2'-methylene bis (4-chlorophenol)
2,2'-methylene bis (3,4,6-trichlorophenol) (hexachlorophene)
2,2'-methylene bis (4-chloro-6-bromophenol)
bis (2-hydroxy-3,5-dichlorophenyl) sulfide
bis (2-hydroxy-5-chlorobenzyl) sulfide The noncationic antibacterial agent is present in the oral composition in an effective antiplaque amount, typically about 0.01–5% by weight although in a mouthwash or liquid dentifrice the amount is generally about 0.01–0.3%, preferably about 0.03–0.3% and more preferably about 0.03–0.1%. The antibacterial agent is substantially water-insoluble, meaning that its solubility is less than about 1% by weight in water at 25° C. and may be even less than about 0.1%.

The preferred halogenated diphenyl ether is triclosan. The preferred phenolic compounds are phenol, thymol, eugenol, and 2,2'-methylene bis(4-chloro-6-bromophenol). The most preferred antibacterial antiplaque compound is triclosan. Triclosan is disclosed in aformentioned U.S. Pat. No. 4,022,880 as an antibacterial agent in combination with an anticalculus agent which provides zinc ions and in German Patent Disclosure 3532860 in combination with a copper compound. In European Patent Disclosure 0278744 it is disclosed in combination with a tooth desensitizing agent containing a source of potassium ion. It is also disclosed as an antiplaque agent in a dentifrice formulated to contain a lamellar liquid crystal surfactant phase having a lamellar spacing of less than 6.0 mm and which may optionally contain a zinc salt in published European Patent Application 0161898 of Lane et al and in a dentifrice containing zinc citrate trihydrate in published European Patent Application 0161899 to Saxton et al.

The antibacterial-enhancing agent (AEA) which enhances delivery of said antibacterial agent to, and retention thereof on, oral surfaces, is employed in amounts effective to achieve such enhancement within the range in the oral composition of about 0.05% to about 4%, preferably about 0.1% to about 3%, more preferably about 0.5% to about 2.5% by weight.

AEA polymeric materials of the present invention include those which can be characterized as having utility as dentifrice adhesives or fixatives or dental cements. For example, U.S. Pat. Nos. 4,521,551 and 4,375,036, each to Chang et al, describe commercially available copolymer of methylvinyl ether-maleic anhydride (Gantrez) as a denture fixative. However, there has not been recognition in the prior art that adhesives, fixatives or cements when applied in water-soluble or water-swellable form together with substantially water-insoluble non-cationic antibacterial antiplaque agents could enhance the antibacterial activity of such agents. Further, in U.S. Pat. No. 4,485,090 to Chang, Gantrez AN copolymer is mentioned among polymeric anionic membrane-forming materials which attach to a tooth surface to form a hydrophobic barrier which reduces elution of a previously applied therapeutic caries prophylactic fluoride compound. Again, there is no recognition that such polymeric material could enhance the antibacterial activity of substantially water-insoluble non-cationic antibacterial antiplaque agents.

This AEA may be a simple compound, preferably a polymerizable monomer, more preferably a polymer, which latter term is entirely generic, including for example oligomers, homopolymers, copolymers of two or more monomers, ionomers, block copolymers, graft copolymers, cross-linked polymers and copolymers, and the like. The AEA may be natural or synthetic, and water insoluble or preferably water (saliva) soluble or swellable (hydratable, hydrogel forming). It has an (weight) average molecular weight of about 100 to about 1,000,000, preferably about 1,000 to about 1,000,000, more preferably about 2,000 or 2,500 to about 250,000 or 500,000.

The AEA ordinarily contains at least one delivery-enhancing group, which is preferably acidic such as sulfonic, phosphinic, or more preferably phosphonic or carboxylic, or salt thereof, e.g. alkali metal or ammonium, and at least one organic retention-enhancing group, preferably a plurality of both the delivery-enhancing and retention-enhancing groups, which latter groups preferably have the formula —$(X)_n$—R wherein X is O, N, S, SO, $SO_2$, P, PO or Si or the like, R is hydrophobic alkyl, alkenyl, acyl, aryl, alkaryl, aralkyl, heterocyclic or their inert-substituted derivatives, and n is zero or 1 or more. The aforesaid "inert-substituted derivatives", are intended to include substituents on R which are generally non-hydrophilic and do not significantly interfere with the desired functions of the AEA as enhancing the delivery of the antibacterial agent to, and retention thereof on, oral surfaces such as halo, e.g. Cl, Br, I, and carbo and the like. Illustrations of such retention-enhancing groups are tabulated below.

| n | X | —$(X)_n$R |
|---|---|---|
| 0 | — | methyl, ethyl, propyl, butyl, isobutyl, t-butyl, cyclohexyl, allyl, benzyl, phenyl, chlorophenyl, xylyl, pyridyl, furanyl, acetyl, benzoyl, butyryl, terephthaloyl, etc. |
| 1 | 0 | ethoxy, benzyloxy, thioacetoxy, phenoxy, carboethoxy, carbobenzyloxy, etc. |
|   | N | ethylamino, diethylamino, propylamido, benzylamino,, benzoylamido, phenylacetamido, etc. |
|   | S | thiobutyl, thioisobutyl, thioallyl, thiobenzyl, thiophenyl, thiopropionyl, phenylthioacetyl, thiobenzoyl, etc. |
|   | SO | butylsulfoxy, allylsulfoxy, benzylsulfoxy, phenylsulfoxy, etc. |
|   | $SO_2$ | butylsulfonyl, allysulfonyl, benzylsulfonyl, phenylsulfonyl, etc. |
|   | P | diethyphosphinyl, ethylvinylphosphinyl, ethylallylphosphinyl, ethylbenzylphosphinyl, ethylphenylphosphinyl, etc. |
|   | PO | diethylphosphinoxy, ethylvinylphosphinoxy, methylallylphosphinoxy, methylbenzyphosphinoxy, methylphenylphosphinoxy, etc. |
|   | Si | trimethysilyl, dimethylbutylsilyl, dimethylbenzylsilyl, dimethylvinylsilyl, dimethylallylsilyl, etc. |

As employed herein, the delivery-enhancing group refers to one which attaches or substantively, adhesively, cohesively or otherwise bonds the AEA (carrying the antibacterial agent) to oral (e.g. tooth and gum) surfaces, thereby "delivering" the antibacterial agent to such surfaces. The organic retention-enhancing group, generally hydrophobic, attaches or otherwise bonds the antibacterial agent to the AEA, thereby promoting retention of the antibacterial agent to the AEA and indirectly on the oral surfaces. In some instances, attachment of the antibacterial agent occurs through physical entrapment thereof by the AEA, especially when the AEA is a cross-linked polymer, the structure of which inherently provides increased sites for such entrapment. The presence of a higher molecular weight, more hydrophobic cross-linking moiety in the cross-linked polymer still further promotes the physical entrapment of the antibacterial agent to or by the cross-linked AEA polymer.

Preferably, the AEA is an anionic polymer comprising a chain or backbone containing repeating units each preferably containing at least one carbon atom and preferably at least one directly or indirectly pendant, monovalent delivery-enhancing group and at least one directly or indirectly pendant monovalent retention-enhancing group geminally, vicitally or less preferably otherwise bonded to atoms, preferably carbon, in the chain. Less preferably, the polymer may contain delivery-enhancing groups and/or retention-enhancing groups and/or other divalent atoms or groups as links in the polymer chain instead of or in addition to carbon atoms, or as cross-linking moieties.

It will be understood that any examples or illustrations of AEA's disclosed herein which do not contain both delivery-enhancing groups and retention enhancing groups may and preferably should be chemically modified in known manner to obtain the preferred AEA's containing both such groups and preferably a plurality of each such groups. In the case of the preferred polymeric AEA's, it is desirable, for maximizing substantivity and delivery of the antibacterial agent to oral surfaces, that the repeating units in the polymer chain or backbone containing the acidic delivery enhancing groups constitute at least about 10%, preferably at least about 50%, more preferably at least about 80% up to 95% or 100% by weight of the polymer.

According to a preferred embodiment of this invention, the AEA comprises a polymer containing repeating units in which one or more phosphonic acid delivery-enhancing groups are bonded to one or more carbon atoms in the polymer chain. An example of such an AEA is poly (vinyl phosphonic acid) containing units of the formula:

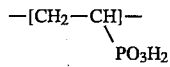

I which however does not contain a retention-enhancing group. A group of the latter type would however be present in poly (1-phosphonopropene) with units of the formula:

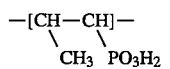

II

A preferred phosphonic acid-containing AEA for use herein is poly (beta styrene phosphonic acid) containing units of the formula:

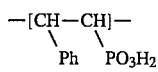  III wherein Ph is phenyl, the phosphonic delivery-enhancing group and the phenyl retention-enhancing group being bonded on vicinal carbon atoms in the chain, or a copolymer of beta styrene phosphonic acid with vinyl phosphonyl chloride having the units of the foregoing formula III alternating or in random association with units of formula I above, or poly (alpha styrerie phosphonic acid) containing units of the formula:

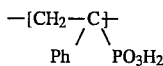  IV in which the delivery—and retention—enhancing groups are geminally bonded to the chain.

These styrerie phosphonic acid polymers and their copolymers with other inert ethylenically unsaturated monomers generally have molecular weights in the range of about 2,000 to about 30,000, preferably about 2,500 to about 10,000, and are, with their methods of preparation disclosed and claimed in concurrently filed application Ser. No. 398,606, which disclosure is incorporated here. Such "inert" monomers do not significantly interfere with the intended function of any copolmyer employed as an AEA herein.

Other phosphonic-containing polymers include, for example, phosphonated ethylene having units of the formula.

where n may for example be an integer or have a value giving the polymer a molecular weight of about 3,000; and sodium poly (butene-4,4-diphosphonate) having units of the formula:

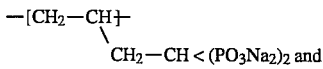  VI poly (allyl bis (phosphonoethyl) amine) having units of the formula:

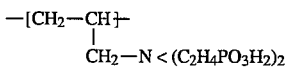  VII

Other phosphonated polymers, for example poly (allyl phosphono acetate), phosphonated polymethacrylate, etc. and the geminal diphosphonate polymers disclosed in EP Publication 0321233 may be employed herein as AEA's, provided of course that they contain or are modified to contain the above-defined organic retention-enhancing groups.

Although not used in the present invention to coact with polyphosphate anticalculus agent, synthetic anionic polymeric polycarboxylate having a molecular weight of about 1,000 to about 1,000,000, preferably about 30,000 to about 500,000, have been used as an inhibitor of alkaline phosphate enzyme in optimizing anticalculus effectiveness of linear molecularly dehydrated polyphosphate salts, as disclosed in U.S. Pat. No. 4,627,977 to Gaffar et al. Indeed, in published British Patent Publication 22 00551, the polymeric polycarboxylate is dislosed as an optional ingredient in oral compositions containing linear molecularly dehydrated polyphosphate salts and substantially water-insoluble noncationic antibacterial agent. It is further observed, in the context of the present invention that such polycarboxylate is markedly effective to enhance delivery and retention of the noncationic antibacterial, antiplaque agent to dental surfaces even when another ingredient with which the polymeric polycarboxylate would coact (that is, molecularly dehydrated polyphosphate) is absent; for instance, when the ingredient with which the polymeric polycarboxylate coacts is especially the noncationic antibacterial agent.

Synthetic anionic polymeric polycarboxylates and their complexes with various cationic germicides, zinc and magnesium have been previously disclosed as anticalculus agents per se in, for example U.S. Pat. No. 3,429,963 to Shedlovsky; U.S. Pat. No. 4,152,420 to Gaffar; U.S. Pat. No. 3,956,480 to Dichter et al; U.S. Pat. No. 4,138,477 to Gaffar; and U.S. Pat. No. 4,183,914 to Gaffar et al. It is to be understood that the synthetic anionic polymeric polycarboxylates so disclosed in these several patents when containing or modified to contain the said retention-enhancing groups are operative as AEA's in the compositions and methods of this invention and such disclosures are to that extent incorporated herein by reference thereto.

The synthetic anionic polymeric polycarboxylates are often employed in the form of their free acids or preferably partially or more preferably fully neutralized water soluble or water swellable (hydratable, gel forming) alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether (maleic anhydride) having a molecular weight (M.W.) of about 30,000 to about 1,000,000, most preferably about 30,000 to about 500,000. These copolymers are available for example as Gantrez, e.g. AN 139 (M.W. 500,000), A.N. 119 (M.W. 250,000); and preferably S-97 Pharmaceutical Grade (M.W. 70,000), of GAF Corporation.

Other AEA operative polymeric polycarboxylates when containing or modified to contain the said retention-enhancing groups, include those disclosed in U.S. Pat. No. 3,956,480 referred to above, such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates disclosed in above referred to U.S. Pat. Nos. 4,138,477 and 4,183,914, when containing or modified to contain retention enhancing groups include copolymers of maleic anhydride with styrene, isobutylene or ethyl vinyl ether, polyacrylic, polyitaconic and polymaleic acids, and sulfoacrylic oligomers of M.W. as low as 1,000, available as Uniroyal ND-2.

Suitable generally are retention-enhancing group-containing polymerized olefinically or ethylenically unsaturated carboxylic acids containing an activated carbon-to-carbon olefinic double bond and at least one carboxl group, that is, an acid containing an olefinic double bond which readily functions in polymerization because of its presence in the monomer molecule either in the alpha-beta position with respect to a carboxl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers ordinarily contain sufficient carboxylic salt groups for water-solubility.

Also useful herein are so-called carboxyvinyl polymers disclosed as toothpaste components in U.S. Pat. No. 3,980,767 to Chown et al; U.S. Pat. No. 3,935,306 to Roberts et al; U.S. Pat. No. 3,919,409 to Perla et al; U.S. Pat. No. 3,911,904 To Harrison, and U.S. Pat. No. 3,711,604 to Colodney et al. They are commercially available for example under the trademarks Carbopol 934, 940 and 941 of B. F. Goodrich, these products consisting essentially of a colloidally water-soluble polymer of polyacrylic acid crosslinked with from about 0.75% to about 2.0% of polyallyl sucrose or polyallyl pentaerythritol as cross linking agent.

The AEA may also comprise natural anionic polymeric polycarboxylates containing retention-enhancing groups. Carboxymethyl cellulose and other binding agents gums and film-formers devoid of the above-defined delivery-enhancing and/or retention-enhancing groups are ineffective as AEA's.

As illustrative of AEA's containing phosphinic acid and/or sulfonic acid delivery enhancing groups, there may be mentioned polymers and copolymers containing units or moieties derived from the polymerization of vinyl or allyl phosphinic and/or sulfonic acids substituted as needed on the 1 or 2 (or 3) carbon atom by an organic retention-enhancing group, for example having the formula —$(X)_n$—R defined above. Mixtures of these monomers may be employed, and copolymers thereof with one or more inert polymerizable ethylenically unsaturated monomers such as those described above with respect to the operative synthetic anionic polymeric polycarboxylates. As will be noted, in these and other polymeric AEA's operative herein, usually only one acidic delivery-enhancing group is bonded to any given carbon or other atom in the polymer backbone or branch thereon. Polysiloxanes containing pendant delivery-enhancing groups and retention enhancing groups may also be employed as AEA's herein. Also effective as AEA's herein are ionomers containing or modified to contain delivery- and retention-enhancing groups. Ionomers are described on pages 546–573 of the Kirk-Othmer Encyclopedia of Chemical Technology, third edition, Supplement Volume, John Wiley & Sons, Inc. copyright 1984, which description is incorporated herein by reference. Also effective as AEA's herein, provided they contain or are modified to certain retention-enhancing groups, are polyesters, polyurethanes and synthetic and natural polyamides including proteins and proteinaceous materials such as collagen, poly (argenine) and other polymerized amino acids.

The synthetic anionic polymeric polycarboxylate component is most often a hydrocarbon with optional halogen and O-containing substituents and linkages as present in for example ester, ether and OH groups, and is employed in the instant compositions in approximate weight amounts of 0.05 to 4% or more, e.g. to about 5%, preferably 0.05 to 3%, more preferably 0.1 to 2%.

Without being bound to a theory, it is believed that the AEA, especially polymeric AEA is most often an anionic film forming material and is thought to attach to tooth surfaces and form a continuous film over the surfaces, thereby preventing bacterial attachment to tooth surfaces. It is possible that the noncationic antibacterial agent forms a complex or other form of association with the AEA, thus forming a film of a complex or the like over tooth surfaces.

The enhanced delivery and film forming property of the AEA and the enhanced delivery and retention of the antibacterial agent on tooth surfaces due to the AEA appears to make tooth surfaces unfavourable for bacterial acumulation particularly since the direct bacteriostatic action of the antibacterial agent controls bacterial growth. Therefore, through the combination of three modes of actions: 1) enhanced delivery, 2) long retention time on tooth surfaces, and 3) prevention of bacterial attachment to tooth surfaces, the oral composition is made efficacious for reducing plaque. Similar antiplaque effectiveness is attained on soft oral tissue at or near the gum line.

In the present invention, the oral composition is a mouthwash or liquid dentifrice and is substantially liquid in character. In a mouthwash preparation the vehicle, in addition, is typically a water-alcohol mixture. Generally, the weight ratio of water to alcohol is in the range of from about 1:1 to about 20:1, preferably about 3:1 to 10:1 and more preferably about 4:1 to about 6:1. The total amount of water-alcohol mixture in this type of preparation is typically in the range of from about 70 to about 99.9% by weight. The alcohol is a non-toxic alcohol such as ethanol or isopropanol. Humectant such as glycerine and sorbitol may be present in amount of about 10–30% by weight. Liquid dentifrices typically contain about 50–85% of water, may contain about 0.5–20% by weight of non-toxic alcohol and may also contain about 10–40% by weight of humectant such as glycerine and/or sorbitol. Reference hereto sorbitol refers to the material typically as available commercially in 70% aqueous solutions. Ethanol is the preferred non-toxic alcohol. The alcohol is believed to assist in dissolving the water-insoluble non-cationic antibacterial agent as, it is believed also does flavoring oil.

As indicated, the noncationic antibacterial agent is substantially water-insoluble. However, in the present invention, with the polycarboxylate present in the mouthwash or liquid dentifrice, organic surface agent, flavoring oil or non-toxic alcohol are believed to aid dissolving the antibacterial agent to assist it to reach soft oral tissue at or near the gums as well as tooth surfaces.

Organic surface-active agents are also used in the compositions of the present invention to achieve increased prophylactic action, assist in achieving thorough and complete dispersion of the antiplaque antibacterial agent throughout the oral cavity, and render the instant compositions more cosmetically acceptable. The organic surface-active material is preferably anionic, nonionic or ampholytic in nature, and it is preferred to employ as the surface-active agent a deterslye material which imparts to the composition detersive and foaming properties. Suitable examples of anionic surfactants are water-soluble salts of higher fatty acid monoglycertde monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxy propane sulfonate, and the substantially saturated higher aliphatic acyl amides of lower aliphatic amino carboxlic acid compounds, such as those having 12 to 16 carbons in the fatty acid, alkyl or acyl radicals, and the like. Examples of the last mentioned amides are N-lauroyl safcosine, and the sodium, potassium, and ethanolamine salts of N-lauroyl, N-myristoyl, or N-palmitoyl safcosine which should be substantially free from soap or similar higher fatty acid material. The use of these sarcosinate compounds in the oral compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions. Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly(ethylene oxide) with fatty acids, fatty alcohols, fatty amides, polyhydric alcohols (e.g. sorbitan monosterate) and polypropyleneoxide (e.g. Pluronic materials).

Surface active agent is typically present in amount of about 0.5–5% by weight, prefereably about 1–2.5%.

If desired, an additional material which assists in dissolving the noncationic antibacterial agent, particularly in the presence of saliva, may be present, to assist effective antiplaque delivery of the antibacterial agent, particularly to soft oral tissues at or near the gume line. Such effective solubilizing agent include humectant polyols such as propylene glycol, dipropylene glycol and hexylene glycol cellosolves such as methyl cellosolve and ethyl cellosolve, vegetable oils and waxes containing at least about 12 carbons in a straight chain such as oliv oil, castor oil and petrolatum and esters such as amyl acetate, ethyl acetate and benzyl benzoate.

Significant amounts of polyethylene glycol particularly of molecular weight of 600 or more should be avoided since polyethylene glycol effectively inhibits the antibacterial activity of the noncationic antibacterial agent. For instance, polyethylene glycol (PEG) 600 when present with triclosan in a weight ratio of 25 triclosan:1 PEG 600 reduces the antibacterial activity of triclosan by a factor of about 16 from that prevailing in the absence of the polyethylene glycol.

When the oral composition is a liquid dentifrice a natural or synthetic thickener or gelling agent is typically present in proportions of about 0.1 to about 10%, preferably about 0.5 to about 5%. A suitable thickener is synthetic hectorite, a synthetic colloidal magnesium alkali metal silicate complex clay available for example as Laponite (e.g. CP, SP 2002,D) marketed by Laporte Industries Limited. Laponite D analysis shows, approximately by weight, 58.00% $SiO_2$, 25.40% MgO, 3.05% $Na_2O$, 0.98% $Li_2O$, and some water and trace metals. Its true specific gravity is 2.53 and it has an apparent bulk density (g./ml. at 8% moisture) of 1.0.

Other suitable thickeners or gelling agents or thickeners include Irish moss, i-carrageenan, gum tragacanth, starch, polyvinylpyrrolidone, hydroxyethypropyl-cellulose, hydroxybutyl methyl cellulose, hydroxypropyl methyl cellulose, hydroxyethyl cellulose (e.g. available as Natrosol), sodium carboxymethyl cellulose and colloidal silica such those available as finely ground Syloid (244) and Sylodent 15.

Generally liquid dentifrices do not contain a polishing agent. However, as described in U.S. Pat. No. 3,506,757 to Salzmann, about 0.3–2.0% by weight of a polysaccharide of high molecular weight in excess of 1,000,000 containing mannose, glucose, potassium glucuronate and acetyl moieties in the approximate ratio of 2:1:1:1, as suspending and thickening agent can be employed in a liquid dentifrice, which then may also contain about 10–20% of a polishing material such as hydrated alumina, dicalcium phosphate dihydrate, calcium pyrophosphate, insoluble sodium metephosphate, anhydrous dicalcium phosphate, calcium carbonate, magnesium carbonate, magnesium oxide, silica, mixtures thereof, and the like.

Many of the so-called "water-insoluble" polishing materials are anionic in character and also include small amounts of soluble material. Thus, insoluble sodium metephosphate may be formed in any suitable manner as illustrated by Thorpe's Dictionary of Applied Chemistry, Volume 9, 4th Edition, pp. 510–511. The forms of insoluble sodium metephosphate known as Madrell's salt and Kurrol's salt are further examples of suite materials. These metephosphate salts exhibit only a minute solubility in water, and therefore are commonly referred to as insoluble metephosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than 1% of the material is larger than 37 microns.

Hydrated alumina is an example of a polishing material which is essentially nonionic in nature. Typically, it is small in particle size, i.e., at least about 85% of the particles are smaller than 20 microns and is such as that classified as gibbsite (alpha alumina trihydrate) and normally represented chemically as $Al_2O_3.3H_2O$ or $Al(OH)_3$. The average particle size of gibbsite is generally about 6 to 9 microns. A typical grade has the following size distribution:

| Microns | Percent |
| --- | --- |
| <30 | 94–99 |
| <20 | 85–93 |
| <10 | 56–67 |
| <5 | 28–40 |

Without being bound to a theory whereby The advantages of this invention are achieved, it is believed that an aqueous vehicle, typically including humectant, is normally solubilized in surfactant micelles in a mouthwash or mobile phase (that is, not including gelling agent and possibly a polishing agent in liquid dentifrice). Such solution during use becomes diluted with saliva but triclosan does not substantially precipitate and may be additionally protected against precipitation by presence of a solubilizing material such as propylene glycol. In this regard it is noted that propylene glycol is widely used in drug delivery systems for its strong interaction with biological membranes. It is expected that triclosan is partitioned from aqueous environment into propylene glycol and surfactant emulsions during use and further that propylene glycol in bulk phase allows greater probability of triclosan emergence out of surfactant micelles, thereby rendering triclosan available for delivery into bacterial and soft surfaces as well as onto tooth surfaces. Similar remarks apply to other water-insoluble noncationic antibacterial agents herein described.

The oral composition mouthwash or liquid dentifrice may also contain an anticaries amount of fluoride ion source sufficient to supply 25 ppm. to 5,000 ppm. of fluoride ions. The fluoride ion source may be present even when the polyphosphate anticalculus agent is not, since it also provides anticaries effectiveness.

The sources of fluoride ions, or fluoride-providing component are well known in the art as anti-caries agents. These compounds may be slightly soluble in water or may be fully water-soluble. It is characterized by its ability to release fluoride ions in water and by substantial freedom from undesired reaction with other compounds of the oral preparation. Among these materials are inorganic fluoride salts, such as soluble alkali metal, alkaline earth metal salts, for example, sodium fluoride, potassium fluoride, ammonium fluoride, calcium fluoride, a copper fluoride such as cuprous fluoride, zinc fluoride, barium fluoride, sodium flourosilicate, ammonium flourosilicate, sodium fluorozirconate, ammonium fluorozirconate, sodium monofluorophosphate, aluminum mono-and di-fluorophosphate, and fluorinated sodium calcium pyrophosphate. Alkali metal and tin fluorides, such as sodium and stannous fluorides, sodium monofluorophosphate (MFP) and mixtures thereof, are preferred.

The amount of fluorine-providing compound is dependent to some extent upon the type of compound, its solubility, and the type of oral preparation, but it must be a non-toxic amount, generally about 0.0005 to about 3.0% in the preparation. In a dentifrice preparation, an amount of such compound which releases up to about 5,000 ppm of F ion by weight of the preparation is considered satisfactory. Any suitable minimum amount of such compound may be used, but it is preferable to employ sufficient compound to release about 300 to 2,000 ppm, more preferably 500 or 800 to about 1,500 ppm of fluoride ion.

Typically, in the cases of alkali metal fluorides, this component is present in an amount up to about 2% by weight, based on the weight of the preparation, and preferably in the range of about 0.05% to 1%. In the case of sodium monofluorophosphate, the compound may e present in an amount of about 0.1–3%, more typically about 0.76%.

It will be understood that, as is conventional, the oral preparations are to be sold or otherwise distributed in suitable labelled packages. Thus a jar of mouthrinse will have a label describing it, in substance, as a mouthrinse or mouthwash and having directions for its use; and a liquid toothpaste will usually be in a collapsible or drip tube, typically aluminum, lined lead or plastic, or other dispenser for metering out the contents, having a label describing it, in substance, as a liquid toothpaste or dentifrice.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired. Significant amounts of zinc, magnesium and other metal salts and materials, generally soluble, which would complex with active components of the instant invention are to be avoided.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, xylitol, sodium cyclamate, perillatrine, AMP (aspartyl phenyl alanins, methyl ester), saccharine and the like. Suitably, flavor and sweetening agents may each or together comprise from about 0.1% to 5% or more of the preparation, each being typically about 0.1–2.5%. Moreover, the flavoring oil is believed co assist in dissolving the antibacterial agent.

In the preferred practice of this invention an oral composition according co this invention such as a mouthwash or liquid dentifrice containing a composition of the present invention is preferably applied regularly to dental enamel such as every day or every second or third day or preferably from 1 to 3 times daily, at a pH of about 4.5 to about 9, generally about 5.5 to about 8, preferably about 6 to 8, for at least 2 weeks up to 8 weeks or more up to lifetime.

The following examples are further illustranive of the nature of the present invention, but it is understood that the invention is not limited thereto. All amounts and proportions referred to herein and in the appended claims are by weight, unless otherwise indicated.

EXAMPLE 1

The mouthrinses below are effective in reducing plaque by increasing the uptake and retention of triclosan oral surfaces.

|  | A Parts | B Parts | C Parts | D Parts | E Parts |
|---|---|---|---|---|---|
| Gantrez S-97 | 0.25 | 0.25 | 0.25 | 0.25 | 0.25 |
| Glycerine | 15.00 | 10.00 | 15.00 | 10.00 | 15.00 |
| Ethanol | — | — | 12.50 | 12.50 | — |
| Propylene glycol | — | 5.00 | — | 5.00 | — |
| Pluronic F108-(Polyoxyethylene/Polyoxypropylene Block Copolymer) | — | 2.00 | — | — | — |
| Sodium Lauryl Sulfate | — | — | 0.20 | 0.20 | 0.20 |
| Triclosan | 0.10 | 0.10 | 0.06 | 0.06 | 0.03 |
| Flavoring oil | 0.40 | 0.40 | 0.40 | 0.40 | 0.40 |
| Water | Q.S. to 100.00 | Q.S. to 100.00 | Q.S to 100.00 | Q.S. to 100.00 | Q.S. to 100.00 |

EXAMPLE 2

The following liquid dentifrices are also effective in reducing plaque by increasing the uptake and retention of triclosan on oral surfaces:

|  | A Parts | B Parts | C Parts |
|---|---|---|---|
| Glycerine | 20.0 | 20.0 | — |
| Gantrez S-97 | 0.3 | 0.3 | 0.3 |
| Polysaccharide.of high molecular weight, the molecule containing mannose, glucose, potassium glucuronate and acetyl moieties in the approximate molar ratio of 2:1:1:1 | 0.8 | — | 1.0 |
| Sodium benzoate | 0.5 | 0.5 | 0.5 |
| Saccharine sodium | 0.5 | 0.5 | 0.5 |
| Water | 61.3 | 73.1 | 71.6 |
| Sodium lauryl sulfate | 3.0 | 3.0 | 3.0 |
| Insoluble sodium metal phosphate | 10.0 | — | 10.0 |
| Anhydrous dicalcium phosphate | 1.0 | — | 2.5 |
| Flavoring oil | 2.5 | 2.5 | 2.5 |
| Ethyl alcohol | — | — | 10.0 |
| Triclosan | 0.1 | 0.1 | 0.1 |

In the foregoing Examples improved results are also achievable when triclosan is replaced with each of phenol, 2,2'-methylene bis (4-chloro-6-Bromophenol), eugenol and thymol, and/or when Gantrez is replaced by other AEA's such as Carbopols (e.g. 934), or styrerie phosphonic acid polymers having molecular weights within the range of about 3,000 to 10,000 such as poly (beta-styrenephosphonic acid), copolymers of vinyl phosphonic acid with beta-styrenephosphonic acid, and poly (alphastyrenephosphonic acid), or sulfoacrylic oligomers, or a 1:1 copolymer of maleic anhydridte with ethyl acrylate.

This invention has been described with respect to certain preferred embodiments and it will be understood that modifications and variations thereof obvious to those skilled in the art are to be included within the purview of this appli-

We claim:

1. Oral composition mouthwash or liquid dentifrice comprising an aqueous vehicle, an effective antiplaque amount of a substantially water insoluble noncationic antibacterial agent, said oral composition comprising at least one of a surface active agent, a flavoring oil and a non-toxic alcohol and about 0.005–4% by weight of an antibacterial-enhancing agent having an average molecular weight of about 100 to 1,000,000 which contains at least one carboxylic delivery-enhancing functional group and at least one organic retention-enhancing group, wherein said delivery-enhancing group enhances delivery of said antibacterial agent to oral tooth and gum surfaces and said retention-enhancing group enhances attachment, adherence or bonding of said antibacterial agent on oral tooth and gum surfaces, wherein said oral composition mouthwash or liquid dentifrice is free of polyphosphate anticalculus agent in an effective anticalculus amount.

2. The oral composition claimed in claim 1 wherein said antibacterial agent is selected from the group consisting of halogenated diphenyl ethers, halogenated salicylanilides, benzoic esters, halogenated carbanilides and phenolic compounds.

3. The oral composition claimed in claim 2 wherein said antibacterial agent is a halogenated diphenyl ether.

4. The oral composition mouthwash or liquid dentifrice claimed in claim 3 wherein said halogenated diphenyl ether is 2,4,4'-trichloro-2'-hydroxyphenyl ether.

5. The oral composition mouthwash or liquid dentifrice claimed in claim 2 wherein said antibacterial agent is a phenolic compound.

6. The oral composition mouthwash or liquid dentifrice claimed in claim 5 wherein said phenolic compound is selected from the group consisting of phenol, thymol, eugenol and 2,2'-methylene bis (4-chloro-6-bromophenol).

7. The oral composition mouthwash or liquid dentifrice claimed in any of claims 1 to 6 wherein said antibacterial agent is present in amount of about 0.01–5% by weight.

8. The oral composition mouthwash or liquid dentifrice claimed in claim 7 wherein said amount of antibacterial agent is about 0.25–0.5%.

9. The oral composition claimed in any of claims 1 to 6 wherein said composition is a mouthwash and said aqueous vehicle contains a non-toxic alcohol and the weight ratio of water to non-toxic alcohol is from about 1:1 to about 20:1.

10. The oral composition mouthwash claimed in claim 9 wherein said non-toxic alcohol is ethanol.

11. The oral composition claimed in any of claims 1 to 6 wherein said oral composition is a liquid dentifrice.

12. The oral composition liquid dentifrice claimed in claim 11 wherein said liquid dentifrice contains about 0.3–2.0% by weight of a polysaccharide of high molecular weight in excess of 1,000,000 containing mannose, glucose, potassium glucuronate and acetyl moieties in the approximate ratio of 2:1:1:1, as suspending and thickening agent.

13. The oral composition liquid dentifrice claimed in claim 12 wherein said liquid dentifrice contains about 10–20% by weight of a polishing material.

14. The oral composition mouthwash or liquid dentifrice claimed in any of claims 1 to 6 wherein said surface active agent is present in amount of about 0.5–5% by weight.

15. The oral composition mouthwash or liquid dentifrice claimed in any of claims 1 to 6 wherein said flavoring oil is present in amount of about 0.1–5% by weight.

16. The oral composition claimed in claim 15 wherein said organic retention-enhancing group comprises the formula $-(X)_n-R$ wherein X is O, N, S, SO, $SO_2$, P, PO or Si, R is hydrophobic alkyl, aryl, alkaryl, alkenyl, acyl, aralkyl, heterocyclic, or inert-substituted derivatives thereof, and n is zero or 1 or more and wherein said antibacterial-enhancing agent is a natural or synthetic monomer or a polymer selected from a group consisting of oligomers, homopolymers, copolymers of two or more monomers, ionomers, block copolymers, graft copolymers and cross-linked polymers and monomers.

17. The oral composition claimed in claim 16 wherein said antibacterial-enhancing agent is a carboxylic polymer containing a plurality of said delivery-enhancing and retention-enhancing groups.

18. The oral composition according to claim 17 wherein said carboxylic polymer comprises a chain containing repeating units each containing at least one carbon atom.

19. The oral composition claimed in claim 18 wherein the unit contains at least one carboxylic delivery-enhancing group and at least one retention-enhancing group bonded to the same, vicinal, or other atoms in the chain.

20. Oral composition mouthwash or liquid dentifrice comprising an aqueous vehicle, an effective antiplaque amount of a substantially water insoluble noncationic antibacterial agent, said oral composition comprising at least one of a surface active agent, a flavoring oil and a non-toxic alcohol and about 0.005–4% by weight of an anionic copolymer of maleic acid or anhydride with another ethylenically unsaturated polymerizable monomer, which copolymer enhances delivery and attachment, adherence or bonding of said antibacterial agent on oral tooth and gum surfaces, wherein said oral composition is free of polyphosphate anticalculus agent in an effective anticalculus amount.

21. The oral composition claimed in claim 20 wherein said other monomer of said copolymer is methyl vinyl ether in a 4:1 to 1:4 molar ratio with the maleic acid or anhydride.

22. The oral composition claimed in either of claims 20 or 21 wherein said copolymer has a molecular weight of about 30,000– 1,000,000.

23. The oral composition claimed in claim 22 wherein the copolymer has an average molecular weight of about 70,000.

24. Oral composition mouthwash or liquid dentifrice comprising an aqueous vehicle, about 0.01–5% of triclosan, at least one member of the group consisting of surface active agents, flavoring oils and non-toxic alcohols, and about 0.05–4% of a copolymer of maleic acid or anhydride with methyl vinyl ether, said composition being free of polyphosphate anticalculus agent in an effect anticalculus amount.

25. The oral composition claimed in any of claims 1 to 6 or 20 to 24 containing a fluoride-providing source.

* * * * *